(12) United States Patent
Fukai

(10) Patent No.: US 9,074,184 B2
(45) Date of Patent: Jul. 7, 2015

(54) REMEDY FOR CHRONIC INFLAMMATION AND ANTIBODY TO BE USED THEREIN

(71) Applicant: TOKYO UNIVERSITY OF SCIENCE EDUCATIONAL FOUNDATION, Tokyo (JP)

(72) Inventor: Fumio Fukai, Tokyo (JP)

(73) Assignee: TOKYO UNIVERSITY OF SCIENCE EDUCATIONAL FOUNDATION, Tokyo (JP)

(*) Notice: Subject to any disclaimer, the term of this patent is extended or adjusted under 35 U.S.C. 154(b) by 226 days.

(21) Appl. No.: 13/678,071

(22) Filed: Nov. 15, 2012

(65) Prior Publication Data

US 2013/0071929 A1 Mar. 21, 2013

Related U.S. Application Data

(63) Continuation of application No. 13/148,233, filed as application No. PCT/JP2010/051639 on Feb. 4, 2010, now abandoned.

(30) Foreign Application Priority Data

Feb. 6, 2009 (JP) ................. 2009-025707

(51) Int. Cl.
  *G01N 33/53* (2006.01)
  *C12N 5/078* (2010.01)
  *C07K 16/18* (2006.01)

(52) U.S. Cl.
  CPC .............. *C12N 5/0634* (2013.01); *C07K 16/18* (2013.01); *C07K 2317/76* (2013.01)

(58) Field of Classification Search
  None
  See application file for complete search history.

(56) References Cited

U.S. PATENT DOCUMENTS 6,440,710 B1 8/2002 Keinan et al.

FOREIGN PATENT DOCUMENTS

| JP | 2002234900 A | 8/2002 |
|---|---|---|
| JP | 2004138489 A | 5/2004 |
| JP | 2004217546 A | 8/2004 |
| JP | 2006-249031 A | 9/2006 |
| WO | WO-2009/089998 A1 | 7/2009 |

OTHER PUBLICATIONS

Castellon et al. Effects of Tenascin-C on Normal and Diabetic Retinal Endothelial Cells in Culture. Castellon et al Investigative Ophthalmology & Visual Science, Aug. 2002, 43(8):2758-2766.*
Saze et al. Apoptosis induction of leukemia cells by the integrin-activating peptide derived from tenascin-C. Peptide Science (2003), Volume Date 2004, 40th, 351-354. Abstract only.*
Koyama et al. Effect of Tenascin-C Deficiency on Chemically Induced Dermatitis in the Mouse. (1998) J. Invest. Dermatol. 111, 930-935.*
Talts et al. Tenascin-C modulates tumor stroma and monocyte/macrophage recruitment but not tumor growth or metastasis in a mouse strain with spontaneous mammary cancer. Journal of Cell Science 112, 1855-1864 (1999).*
Clark et al. Tenascin Supports Lymphocyte Rolling. JCB, 137:755-765, 1997.*
Hauzenberger et al. Tenascin-C inhibits β1 integrin-dependent T lymphocyte adhesion to fibronectin through the binding of its fnIII 1-5 repeats to fibronectin. Eur. J. Immunol. 1999. 29: 1435-1447.*
Saito et al. Apoptotic Death of Hematopoietic Tumor Cells through Potentiated and Sustained Adhesion to Fibronectin via VLA-4. J. Biol. Chem. 2010, 285:7006-7015, published online Dec. 10, 2009.*
Onoda et al. Transendothelial migration of T-lymphocytic cells induced by tenascin-C. Connective Tissue Research, (Feb. 2011) vol. 52, No. 1, pp. 68. Abstract No. P13.*
Database WPI Thomson Scientific London, GB, XP002702808, cited in Extended European Search Report for corresponding European Application: EP10738603 dated, Jul. 25, 2013.*
Extended European Search Report for corresponding European Application: EP10738603 dated, Jul. 25, 2013.
Balza et al., Production and characterization of monoclonal antibodies specific for different epitopes of human tenascin, FEBS, 332:39-43 (1993).
Chiquet-Ehrismann et al., tenascins: regulation and putative fuctions during pathological stress, J. Pathol, 200:488-499 (2003).
Dubck et al., Detection of Tenascin-C isoforms in colorectal mucosa, ulcerative colitis, carcinomas and liver metastases, Int. J. Cancer, 82:477-483 (1999).
Gullberg et al., Tenascin-C expression correlates with macrophage invasion in Duchenne muscular dystophy and in myositis, Neuromuscular Disorders, 7:39-54 (1997).
Hasegawa et al., Tenascin-C concentration in synovial fluid correlates with radiographic progression of knee osteoarthritis, J. Rheumatology, 31:10:2021-2026 (2004).
International Search Report for PCT/JP2010/051639 dated Apr. 13, 2010.
Matsunaga et al., Potentiated activation of VLA-4 and VLA-5 accelerates proplatelet-like formation in megakaryocytes, Am. Soc. Hematology, Abstract 2585, 53rd ASH Annual Meeting and Exposition (2010).
Saito et al., A peptide derived from Tenascin-C induces β1 integrin activation through syndecan-4, J. Biol. Chem., 282:34929-34937 (2007).
Saito et al., Inhibition of angiogenesis by a Tenascin-C peptide which is capable of activating beta1-integrins, Biol. Pharm. Bull., 31:1003-1007 (2008).
Tsunoda et al., Involvement of large Tenascin-C splice variants in breast cancer progression, Am. J. Pathology, 162:1857-1867 (2003).

* cited by examiner

*Primary Examiner* — Maher Haddad
(74) *Attorney, Agent, or Firm* — Marshall, Gerstein & Borun LLP

(57) ABSTRACT

The invention provides a remedy for chronic inflammation and an anti-TNIIIA2 antibody to be used therein. The remedy includes an antibody recognizing TNIIIA2, that is a peptide derived from a partial sequence A2 of a human tenascin-C fibronectin III-like repetitive sequence and having the amino acid sequence RSTDLPGLKAATHYTITIRGVC (SEQ ID NO: 1).

4 Claims, 1 Drawing Sheet

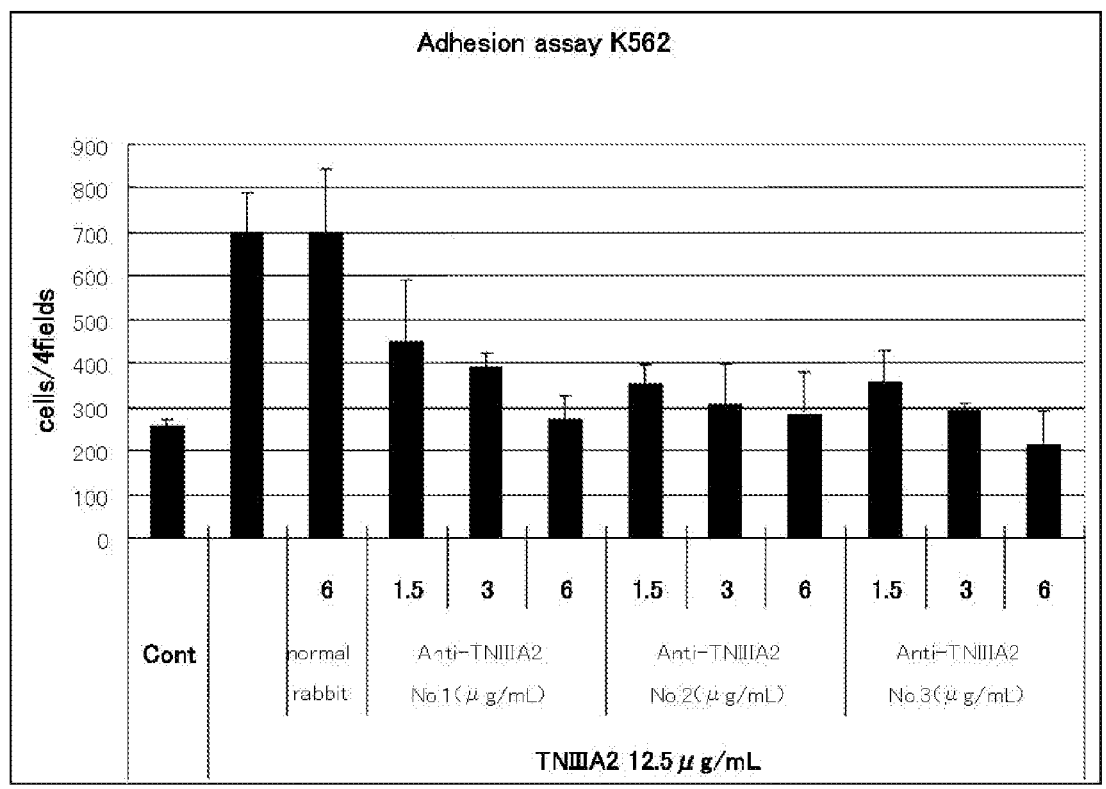

SEQUENCE LISTING

```
<160> NUMBER OF SEQ ID NOS: 3

<210> SEQ ID NO 1
<211> LENGTH: 22
<212> TYPE: PRT
<213> ORGANISM: Homo sapiens

<400> SEQUENCE: 1

Arg Ser Thr Asp Leu Pro Gly Leu Lys Ala Ala Thr His Tyr Thr Ile
1               5                   10                  15

Thr Ile Arg Gly Val Cys
            20

<210> SEQ ID NO 2
<211> LENGTH: 8
<212> TYPE: PRT
<213> ORGANISM: Homo sapiens

<400> SEQUENCE: 2

Tyr Thr Ile Thr Ile Arg Gly Val
1               5

<210> SEQ ID NO 3
<211> LENGTH: 12
<212> TYPE: PRT
<213> ORGANISM: Artificial
<220> FEATURE:
<223> OTHER INFORMATION: synthesised epitope

<400> SEQUENCE: 3

Cys Ala Thr His Tyr Thr Ile Thr Ile Arg Gly Val
1               5                   10
```

REMEDY FOR CHRONIC INFLAMMATION AND ANTIBODY TO BE USED THEREIN

BACKGROUND OF THE INVENTION

1. Technical Field

The present invention relates to a remedy for chronic inflammation and a novel antibody to be used therein.

2. Background Art

The expression of tenascin-C is rarely observed in healthy cells, except for the immune system. Expression of tenascin-C is induced under pathological conditions such as inflammation and tumor growth.

As a method for detecting tenascin-C, some anti-tenascin-C antibodies have been known (for example, see JP-A Nos. 2004-217546 and 2002-234900). An arthritis diagnosis method using tenascin-C as a marker has been also known (for example, see JP-A-2004-138489).

A polypeptide which forms tenascin-C includes an epidermal growth factor-like domain, a fibronectin (FN) III-like domain and a fibrinogen-like domain. Among them, it has been known that the FN III-like domain includes a continuation between 8 basic types of repetitive sequences (1 to 8) and 9 types of repetitive sequences to be spliced (A1, A2, A3, A4, B, AD2, AD1, C and D), which are inserted between the fifth and the sixth sequences of the 8 basic types thereof. These repetitive sequence sites to be spliced are those easily cut by matrix metalloproteinases (MMP), and a peptide produced by a cut in tenascin-C by MMP are thought as having various functions.

On the other hand, it has been known that, in chronic inflammation, immune cells including monocytes such as macrophages and lymphocytes infiltrate from the blood vessels into the vascular endothelium and penetrate through the vascular basement membrane to gather at an inflammatory site. Such an immune cell infiltration at the inflammatory site is regulated by the interaction between immune cells, vascular endothelial cells and extracellular matrixes via adhesion molecules, integrins, on the immune cell membrane. It has been known that the integrins exist in two conformations, the active form and the inactive form and only the active form of integrins can adhere to extracellular matrixes.

A peptide derived from the A2 domain of the FNIII-like domain of tenascin-C (hereinafter may be referred to as "TNIIIA2") has been known as a peptide causing the activation of the integrins (for example, see J. Biol. Chem., Vol. 282, pp. 34929-34937 (2007)).

However, no details have been given as to the roles of tenascin-C and the peptide derived therefrom in inflammatory sites, and in particular, there has been obtained no clear finding regarding their relationship with chronic inflammation. Further, there are cases that the effects of conventionally-known anti-tenascin-C antibodies against inflammation are inconsistent depending on the site.

SUMMARY

An object of the present invention is to provide a novel remedy effective against chronic inflammation.

A first aspect of the present invention provides an anti-TNIIIA2 antibody recognizing a peptide derived from a partial sequence A2 of a human tenascin-C fibronectin III-like repetitive sequence. The antibody preferably recognizes a peptide having the amino acid sequence of SEQ ID NO: 1.

A second aspect of the present invention provides an immune cell vascular infiltration inhibitor including the antibody.

A third aspect of the present invention provides a cell death inducer for inflammatory cells, including the antibody.

A fourth aspect of the present invention provides a chronic inflammation remedy including the antibody.

The present invention can provide the novel remedy against chronic inflammation.

BRIEF DESCRIPTION OF DRAWINGS

FIG. 1 is a view showing the inhibition effects of anti-human TNIIIA2 antibodies against cell adhesion induced by a peptide TNIIIA2, according to Example 1 of the invention.

DESCRIPTION OF EMBODIMENTS

An antibody according to the invention is an anti-TNIIIA2 antibody recognizing a peptide derived from a partial sequence A2 of a human tenascin-C fibronectin III-like repetitive sequence.

The antibody recognizes the peptide (TNIIIA2) derived from the partial sequence A2 present in the human tenascin-C fibronectin III-like repetitive sequence. The antibody selectively binds to the TNIIIA2, thereby inhibiting immune cell infiltration that can be induced by the TNIIIA2.

The present inventor found that the peptide TNIIIA2 derived from human tenascin-C is associated with the infiltration of immune cells and a cell death-inducing mechanism for inflammatory cells in inflammation sites. The invention is based on this finding.

In the present description, the term "step" encompasses not only independent steps but a case in which even if a step cannot be clearly distinguished from any other step, as long as an effect expected from the step is achieved.

Additionally, in the present description, the numerical range indicated by using "to" refers to a range including respective values presented before and after "to" as a minimum and a maximum, respectively.

Hereinafter, the invention will be described.

The anti-TNIIIA2 antibody of the invention is not specifically limited as long as the antibody can recognize the peptide (TNIIIA2) derived from the partial sequence A2 of the human tenascin-C FNIII-like domain. The anti-TNIIIA2 antibody may be a monoclonal antibody or a polyclonal antibody.

The TNIIIA2 is a peptide composed of 22 amino acids: RSTDLPGLKAATHYTITIRGVC (SEQ ID NO: 1) (See J. Biol. Chem., Vol. 282, pp. 34929-34937 (2007)). The anti-TNIIIA2 antibody of the invention is the antibody that recognizes the TNIIIA2, in which at least a part of the amino acid sequence of the TNIIIA2 shown in SEQ ID NO: 1 is an epitope. The epitope recognized by the anti-TNIIIA2 can be any as long as it is a partial peptide including an amino acid sequence: YTITIRGV (SEQ ID NO: 2).

The peptide to be used to produce the antibody that recognizes the TNIIIA2, namely the peptide (a target peptide) recognized by the anti-TNIIIA2 antibody can be any peptide as long as the peptide includes the sequence of SEQ ID NO: 2, and in embodiments it may be a peptide having the entire length (SEQ ID NO: 1). From the viewpoint of improving antigenicity and stability, a linker function or one or more compounds having a linker function (for example, an amino acid) may be added to the peptide having the amino acid sequence of SEQ ID NO: 2. Examples of such an additional amino acid include amino acids capable of adding an amino acid to be bound to a carrier protein to the peptide having the amino acid sequence of SEQ ID NO: 2, such as cysteine, acidic amino acids or basic amino acids. From the viewpoint of antibody production efficiency, it may be more preferable that the target peptide has an amino acid sequence: CATH-TITIRGV (SEQ ID NO: 3).

The antibody recognizing the TNIIIA2 can be prepared using the target peptide by a usually-conducted method.

For example, when the antibody is a polyclonal antibody, it may be obtained in the following manner. Any of the amino acid sequences of SEQ ID NOs: 1 to 3 or a mixture thereof is used as the target peptide. The target peptide is used to immunize a small animal such as a rabbit to obtain serum. The antibody is then prepared by purification thereof from the obtained serum by using a known antibody-purifying means, such as ammonium sulfate precipitation, protein A, protein G columns, DEAE ion-exchange chromatography, or affinity columns prepared by coupling the specific peptide.

Alternatively, when the antibody is a monoclonal antibody, it may be obtained in the following manner. Any small animal such as a mouse is immunized with the target peptide. A spleen is taken out of the mouse and crushed to isolate cells. The spleen cells are fused with mouse myeloma cells by using a reagent such as polyethylene glycol to form fused cells (hybridomas). Clones which produce antibodies binding to the target peptide are selected from hybridomas. Next, the selected hybridomas are transplanted in the peritoneal cavity of a mouse to collect ascitic fluid from the mouse. The obtained monoclonal antibody is purified by, for example, ammonium sulfate precipitation, protein A, protein G columns, DEAE ion-exchange chromatography or affinity columns prepared by coupling the specific peptide, so as to prepare the antibody.

The target peptide may be used in immunization in a form of a fusion protein in which the by target peptide is fused with a known carrier protein in view of improving antigenicity. Any known molecule used for this purpose can be used as such a carrier protein without any specific restriction, and examples of the carrier protein include KLH, GST and BSA.

The immune cells the infiltration of which is inhibited by the anti-TNIIIA2 antibody are not specifically restricted as long as they are immune cells the infiltration of which is observed in inflammatory sites. Examples of such immune cells include neutrophils, eosinophils, basophils, monocytes, lymphocytes (including plasma cells) and combinations of two or more kinds thereof.

Not being restricted by any specific theory, it is expected that the anti-TNIIIA2 antibody can inhibit the adhesion of immune cells to an extracellular matrix (for example, fibronectin or the like) by hampering the activation of integrins expressed on the immune cell surface induced by tenascin-C or the like. Therefore, the use of the anti-TNIIIA2 antibody may inhibit occurrence of immune cell infiltration across the vascular endothelium.

In addition, at an inflammatory site in chronic inflammation, activated resident immune cells or immune cell infiltrate (these cells are sometimes generically called "inflammatory cells") are known to exist for a longer period of time than usual. The anti-TNIIIA2 antibody can induce the cell death of such inflammatory cells, thereby inhibiting their long-term existence.

A chronic inflammation remedy according to the invention includes at least the anti-TNIIIA2 antibody.

Inclusion of the anti-TNIIIA2 antibody may allow for the inhibition of immune cell infiltration into an inflammatory site and may also allow for the induction of cell death of the inflammatory cells to inhibit the longer existence of the inflammatory cells, whereby chronic inflammation can be treated.

Subjects of treatment with the chronic inflammation remedy may be preferably mammals, and more preferably humans.

The chronic inflammation remedy according to the invention may be administered orally or parenterally, and systemically or locally. Examples of the selectable administration method include intravenous injection such as drip infusion, intramuscular injection, intraperitoneal injection, subcutaneous injection, suppository, enema, oral enteric tablet and the like. The administration method can be selected as appropriate, depending on patients' age and condition of disease. In addition, the amount of administration can also be selected as appropriate, depending on patients' age, condition of disease and the like.

The chronic inflammation remedy may further include a carrier and/or an additive that are pharmaceutically acceptable in accordance with the administration route. Examples of such a carrier and an additive include water, pharmaceutically acceptable organic solvents, collagen, polyvinyl alcohol, polyvinyl pyrrolidone, carboxyvinyl polymer, carboxymethyl cellulose sodium, sodium polyacrylate, sodium alginate, water-soluble dextran, carboxymethyl starch sodium, pectin, methyl cellulose, ethyl cellulose, xanthan gum, gum arabic, casein, gelatin, agar, diglycerin, propylene glycol, polyethylene glycol, Vaseline, paraffin, stearyl alcohol, stearic acid, human serum albumin (HSA), mannitol, sorbitol, lactose and surfactants acceptable as pharmaceutical additives. The additives to be used may be selected as appropriate from the above examples in accordance with the dosage form, but not limited thereto.

An immune cell infiltration inhibitor according to the invention includes at least the anti-TNIIIA2 antibody.

Inclusion of the anti-TNIIIA2 antibody may allow for the inhibition of infiltration of immune cells into the vascular endothelium and effects such as chronic inflammation inhibition or the like can be exhibited.

The immune cell infiltration inhibitor may further include any other component if needed. The carriers and additives pharmaceutically acceptable in the chronic inflammation remedy may be similarly used as such other components.

A cell death inducer for inflammatory cells according to the invention includes at least the anti-TNIIIA2 antibody. Inclusion of the anti-TNIIIA2 antibody may allow for the induction of cell death of inflammatory cells at an inflammatory site, thereby inhibiting their long-term existence and to exhibits effects such as alleviation of symptoms due to chronic inflammation.

The cell death inducer for inflammatory cells may further include any other component if needed. The carriers and additives pharmaceutically acceptable in the chronic inflammation remedy may be similarly used as such other components.

The invention further includes a method for treating or inhibiting chronic inflammation, the method including administration of the remedy including the anti-TNIIIA2 antibody to patients who have or may develop chronic inflammation. Herein, any improvement in symptoms is included in the scope of the "treating chronic inflammation", and thus alleviation of symptoms and inhibition of advances in severity are also included therein. Symptoms of chronic inflammation or symptoms occurring due to inflammation can be inhibited, reduced or alleviated thereby.

The amount of administration in patients may be different depending on the dosage form of a remedy to be applied, patients' sex, age, symptoms and the like or combinations thereof. In general, administration can be done by intravenous injection, intramuscular injection, intraperitoneal injection, subcutaneous injection, suppository, enema and oral enteric tablet, and preferably by intravenous injection.

The method of administration to patients are different depending on the dosage form of a remedy to be applied, patients' sex, age, symptoms and the like or combinations thereof, and, in general, examples of the administration method can include intravenous injection, intramuscular injection, intraperitoneal injection, subcutaneous injection, suppository, enema and oral enteric tablet. From these administration methods, an appropriate method may be selected depending on the condition of the patient. The effective dose of the antibody in treatment may vary depending on the level of symptom and the condition of the patient. In embodiments, it may be in a range of from approximately 0.1 mg/kg weight to approximately 50 mg/kg weight, but not limited thereto. In addition, the frequency of administration may be set, for example, in a range of twice per daily to once per week, but not limited thereto.

EXAMPLES

Hereinafter, the invention will be described by way of Examples, but the invention is not limited to these Examples. Unless specifically stated otherwise, "%" is based on mass.

Example 1

<Production of Anti-human TNIIIA2 Antibody>

A peptide having the amino acid sequence of SEQ ID NO: 3 was synthesized by a usual method. The synthesized peptide as hapten was fused with KLH, and the obtained fusion peptide was used as an antigenic peptide. Immunization was conducted in accordance with a usual method using rabbits. The mixture including a target antibody obtained was purified by a usual method.

In the manner as above, three kinds (No. 1 to No. 3) of polyclonal antibodies (anti-human TNIIIA2 antibodies) against the human TNIIIA2 were obtained.

<Evaluation of Antibody Activity>

Antibody activity of the anti-human TNIIIA2 polyclonal antibodies obtained above were evaluated as follows by using, as indicators, their inhibition effects against cell adhesion induced by the human TNIIIA2. The results are shown in Table 1.

Using RPMI 1640 (20% FBS added) as a cell culture medium, KOP 2.16 cells (a mouse bone marrow-derived vascular endothelial cell line) were seeded in each well of a 96-hole plate at a density of $5 \times 10^4$ cells/200 μL/well to be cultured at 37° C. and 5% $CO_2$ for 4 hours. After 100 μL of the culture supernatant was removed and 100 μL of 20% TCA solution was added, the cells were allowed to stand at 4° C. overnight or at room temperature for 1 hour to be solid-phased. The plate was washed 5 times with PBS, once with RPMI 1640 (20% FBS added) and once with PBS in this order to produce a 96-hole plate with each well coated with KOP 2.16 cells.

Into each well of the 96-hole plate coated with KOP 2.16 cells obtained above was added RPMI 1640 (20% FBS added) containing 12.5 μg/mL of the human TNIIIA2. The anti-human TNIIIA2 antibodies (No. 1 to No. 3) obtained above were added such that their concentrations were 1.5 μg/mL, 3μg/mL and 6μg/mL, respectively, and then, K562 cells (a leukemia cell line) were seeded in each well at the density of $1.5 \times 10^4$ cells/well to be cultured at 37° C. and 5% $CO_2$ for 1 hour.

Following the addition of formalin, the cells were allowed to stand at room temperature for 1 hour to be immobilized.

Then, the plate was washed three times with PBS and stained with Lily Mayer's Hematoxylin. The stained cells were observed with an optical microscope to count adherent cells in a predetermined visual field.

FIG. 1 indicates that the normal rabbit IgG does not inhibit cell adhesion induced by the human TNIIIA2, whereas the anti-human TNIIIA2 antibodies dose-dependently inhibit cell adhesion. In addition, all of the anti-human TNIIIA2 antibodies of No. 1 to No. 3 are shown to exhibit similar degrees of antibody activity. Further, the anti-human TNIIIA2 antibodies did not exhibit inhibition effect against cell adhesion induced by magnesium ion.

The above results show that the anti-human TNIIIA2 antibody of the invention may specifically bind to the human TNIIIA2 to inhibit its function.

Example 2

<Evaluation 1 of Infiltration Inhibiting Properties>

The inhibition of infiltration of Jurkat cells (a T cell-based cell line) into the vascular endothelium by the anti-human TNIIIA2 antibody was evaluated as follows.

Into each well of a 96-hole plate, human tenascin-C at a concentration of 5 μg/mL was added, and the cells were incubated at 37° C. for 1 hour. The plate was blocked by adding BSA at a concentration of 2.5 mg/mL and incubating at 37° C. for 1 hour. The plate was washed three times with PBS to obtain an assay well plate with each well coated with human-tenascin C.

Next, into each well of the assay well plate, KOP 2.16 (the mouse bone marrow-derived vascular endothelial cell line) suspended in a DMEM (+) culture medium was seeded so as to be the condition of $5.0 \times 10^4$ cells/well and cultured at 37° C. and 5% $CO_2$ for 3 hours. Thereby, a single layer composed of the KOP 2.16 cells was formed on the wells coated with human tenascin-C.

A normal rabbit IgG or the anti-human tenascin-C antibody was added to a suspension of Jurkat cells such that its concentration was 20 μg/mL. The resulting cells were gently seeded on the single layer composed of the KOP 2.16 cells at a density of $.1.0 \times 10^4$ cells/well and cultured at 37° C. and 5% $CO_2$ for 3 hours.

After adding formalin and allowing to stand at room temperature for more 1 hour to be immobilized, the cells were washed three times with PBS (−) and stained with Lily Mayer's Hematoxylin. Under an optical microscope (at 200-fold magnification), the numbers of infiltration in predetermined four fields were counted concerning each three wells and an arithmetic average value thereof was determined as an infiltration count.

The infiltration count in a case without adding the human tenascin-C were similarly calculated and was used as a background to subtract from the infiltration count of the human tenascin-C-added sample, whereby obtained infiltration counts is shown in Table 1. Further, the ratio of a difference between the infiltration count of a sample using the normal rabbit IgG and that of the sample using the anti-human TNIIIA2 antibody to the infiltration count of the sample using the normal rabbit IgG was calculated as an infiltration inhibition rate (%).

In addition, the inhibition of THP-1 infiltration into the vascular endothelium by the anti-human TNIIIA2 antibody was evaluated in the same manner as above, except that THP-1 (a monocytes-like cell line) was used instead of the Jurkat cells. The results are shown in Table 1.

TABLE 1

|  | Jurkat | THP-1 |
| --- | --- | --- |
| Normal rabbit IgG | 27 | 41 |
| Anti-human TNIIIA2 antibody | 7 | 1 |
| Infiltration inhibition rate (%) | 74% | 98% |

Table 1 indicates that the anti-human TNIIIA2 antibody can effectively inhibit the infiltration of T-lymphocyte cells or monocytes-like cells into the vascular endothelial layer induced by human tenascin-C.

Example 3

<Evaluation 2 of Infiltration Inhibiting Properties>

The infiltration inhibition effect of the anti-human TnIIIA2 antibody obtained in Example 1 was compared with those of another antibody 4F10TT and a normal rabbit IgG, against human tenascin-C as follows.

The 4F10TT is a rabbit IgG antibody that recognizes a peptide sequence of the epithelium growth factor-like domain of human tenascin-C. The 4F10TT used here was obtained from Immuno-Biological Laboratories Co., Ltd (Tsunoda T. et al., Am J Pathol 162: 1857-1867, 2003; Sato A. et al., J Am Coll Cardiol 47: 2319-2325, 2006).

The count of Jurkat cells which infiltrated into the single layer of the KOP 2.16 cells was measured in the same manner as in Example 2 except that the above antibodies were respectively used.

The infiltration count in a case without adding any antibody was similarly counted. The ratio of the infiltration count of each case of the addition of the normal mouse IgG (normal IgG), the addition of the 4F10TT, and the addition of the anti-human TNIIIA2 antibody to the infiltration count obtained without adding any antibody were calculated. The results are shown in Table 2 ("Coated TNC").

Additionally, the cell infiltration inhibition effect of each antibody was evaluated in the same manner as above, except that, instead of the assay plate with each well coated with human tenascin-C, an uncoated 96-hole plate was prepared and human tenascin-C was added at a concentration of 2µg/mL to bring the total volume per well to 100 µL. The results are shown in Table 2 ("Soluble TNC").

TABLE 2

| Antibody | Coated TNC | Soluble TNC |
| --- | --- | --- |
| — | 1 | 1 |
| Normal IgG | 1.05 | 1.05 |
| 4F10TT | 1.04 | 1.07 |
| Anti-TNIIIA2 | 0.74 | 0.84 |

The results of Table 2 indicate that the cell infiltration inhibition effects of the antibodies recognizing the human tenascin-C-derived peptide differ from each other, and the anti-TNIIIA2 antibody shows a remarkable cell infiltration inhibition effect as compared to the 4F10TT.

Example 3

<Evaluation of Long-term Existence Inhibiting Properties>

The effect of the anti-human TNIIIA2 antibody on changes in viable macrophage cell counts over time in the presence of human tenascin-C was evaluated as follows.

THP-1 cells were cultured in a complete medium, to which PMA was added at a concentration of 10 ng/mL, at 37° C. and 5% $CO_2$ for 24 hours to be induced to differentiate into macrophages (hereinafter, the differentiated THP-1 is referred to as "PMA-THP-1").

Into each well of a 96-hole plate, fibronectin (FN) was added at a concentration of 5 µg/mL, and the plate was incubated at 37° C. for 1 hour. The plate was blocked by adding BSA at a concentration of 2.5 mg/mL and incubating at 37° C. for 1 hour, and washed three times with PBS to obtain a plate with FN-coated each well.

Into the FN-coated wells, an RPMI 1640 (serum-free) culture medium, to which human tenascin-C was added such that its final concentration was 2 µg/mL, was added, and a normal rabbit IgG, the 4F10TT antibody or the anti-human TNIIIA2 antibody was further added to bring its final concentration to 50 µg/mL. Herein, PMA-THP-1 cells were seeded to bring the density to $2 \times 10^4$ cells/well to $2.5 \times 10^4$ cells/well and cultured at 37° C. and 5% $CO_2$ for 24 hours.

Using a cell counting kit (manufactured by DOUJIN Co.) based on the WST method, cell counts were measured to calculate the ratio (viable cell count ratio) of post-culture viable cell counts (day 2) to viable cell counts upon seeding (day 0). The results are shown in Table 3.

TABLE 3

|  | Antibody | Cell count ratio | |
| --- | --- | --- | --- |
| Day 0 |  | 1 | |
| Day 2 | — | 1.52 | 1 |
|  | Normal IgG | 1.48 | 0.97 |
|  | 4F10TT | 1.57 | 1.03 |
|  | Anti-TNIIIA2 | 0.93 | 0.61 |

Table 3 shows the increase of the macrophages in the presence of human tenascin-C. On the contrary, it is shown that, when the anti-human TNIIIA2 antibody is added, increase in the macrophages was inhibited (the ratio of the cell count thereof to that of no antibody-addition sample is 0.61), and the viable cell count decreased (the ratio of the cell count thereof to that measured upon seeding is 0.93). In other words, it is found that the anti-human TNIIIA2 antibody can inhibit long-term existence of the macrophages in the presence of human tenascin-C.

It was observed that the decrease in the viable cell count by the anti-human TNIIIA2 antibody was due to cell death.

It is understood from the above that the anti-human TNIIA2 antibody of the invention may inhibit immune cell infiltration into the vascular endothelium and may induce the cell death of inflammatory cells in the presence of human tenascin-C.

The disclosure of Japanese Patent Application No. 2009-025707 filed on Feb. 6, 2009 is incorporated herein by reference in its entirety.

All documents, patent applications and technical standards described in the present description are incorporated herein by reference to the same extent as if each individual document, patent application and technical standard were specifically and individually indicated to be incorporated by reference.

The invention claimed is:

1. A method for inducing cell death of an inflammatory cell in vitro, the method comprising applying to the inflammatory cell in vitro, an inducer comprising an antibody that recognizes a peptide derived from a partial sequence A2 of human Tenascin-C fibronectin III-like repetitive sequence, wherein the peptide consists of the amino acid sequence of SEQ ID NO: 2 or the amino acid sequence of SEQ ID NO: 1, wherein the inflammatory cell is a macrophage which is differentiated from a monocyte cell by PMA and that exists in a presence of a human Tenascin-C.

2. A method for inducing cell death of an inflammatory cell in vitro, the method comprising applying to the inflammatory cell in vitro, an inducer comprising an antibody that recognizes a peptide derived from a partial sequence A2 of human Tenascin-C fibronectin III-like repetitive sequence and that recognizes an antigen comprising the peptide, the antigen being a fusion protein consisting of a hapten and a carrier protein, wherein the hapten is a peptide derived from a partial sequence A2 of human Tenascin-C fibronectin III-like repetitive sequence consisting of the amino acid sequence of SEQ ID NO: 2 or the amino acid sequence of SEQ ID NO: 1, wherein the inflammatory cell is a macrophage which is differentiated from a monocyte cell by PMA and that exists in a presence of a human Tenascin-C.

3. The method of claim 1, wherein the monocyte cell is a THP-1.

4. The method of claim 2, wherein the monocyte cell is a THP-1.

* * * * *